United States Patent
Olmarker

(10) Patent No.: US 7,427,589 B2
(45) Date of Patent: Sep. 23, 2008

(54) USE OF CYTOKINE INHIBITORS

(75) Inventor: Kjell Olmarker, Mölndal (SE)

(73) Assignee: Pharmasurgics in Sweden AB, Göteborg (SE)

( * ) Notice: Subject to any disclaimer, the term of this patent is extended or adjusted under 35 U.S.C. 154(b) by 87 days.

(21) Appl. No.: 10/092,919

(22) Filed: Mar. 8, 2002

(65) Prior Publication Data

US 2003/0176332 A1    Sep. 18, 2003

(30) Foreign Application Priority Data

Mar. 5, 2002  (SE) .................................... 0200667

(51) Int. Cl.
*A61K 38/00*   (2006.01)

(52) U.S. Cl. ........................................ 514/2

(58) Field of Classification Search ................ 435/7.1, 435/325, 320; 530/350; 514/2, 6, 12, 152; 424/145.1
See application file for complete search history.

(56) References Cited

U.S. PATENT DOCUMENTS

| 5,196,430 | A | 3/1993 | Mandrell et al. |
| 5,994,376 | A | 11/1999 | Freyne et al. |
| 6,348,602 | B1 | 2/2002 | Fowler et al. |
| 2002/0072596 | A1* | 6/2002 | Ruben et al. ............... 536/23.5 |

FOREIGN PATENT DOCUMENTS

| WO | WO 89/05145 | 6/1989 |
| WO | WO 98/06715 | 2/1998 |
| WO | WO 01/57018 | 8/2001 |
| WO | WO 01/58469 | 8/2001 |

OTHER PUBLICATIONS

STN International, File ZCAPLUS, Accession No. 2002: 199887, Document No. 136:323691, Kaser, Arthur et al., "*Infliximab in Severe Steroid-Refractory Ulcerative Colitis: A Pilot Study*", & Wiener Klinische Wochenschrift (2001), 113(23-24), 930-933.
STN International, File MEDLINE, Accession No. 2000046083, Document No. 20046083, Heller T. et al., "*Treatment of Severe Esophageal Crohn's Disease With Infliximab*", & Inflammatory Bowel Diseases, (Nov. 1999) 5 (4) 279-82.
STN International, File MEDLINE, Accession No. 2001011857, Document No. 20409486, Jojic N., [*Pharmacotherapy of Inflammatory Bowel Disease*]. "*Farmakoterapija Inflamatornih Bolesti Creva*", & Acta Chirurgica Jugoslavica, (2000) 47 (1-2) 51-5.
STN International, File MEDLINE, Accession No. 2001419273, Document No. 21360250, Blam M.E., "*Integrating Anti-Tumor Necrosis Factor Therapy in Inflammatory Bowel Disease: Current and Future Perspectives*", American Journal of Gastroenterology, (Jul. 2001) 96(7) 1977-97.
STN International, File MEDLINE, Accession No. 2001553668, Document No. 21486185, Travis S.P. et al., "*Treatment of Intestinal Behcet's Syndrome With Chimeric Tumour Necrosis Factor Alpha Antibody*", & Gut, (Nov. 2001) 49 (5) 725-8.
Black L.E. "Pharmacology review of infliximab BLA"—May 21, 1998—found at internet address: http://www.fda.gov/cder/biologics/review/inflcen082498r4.pdf.
Rekdal et al., "Construction and synthesis of Lactoferricin Derivatives with Enhanced Antibacterial Activity", *Journal of Peptide Science*, 1999, pp. 32-45, vol. 5, University of Tromsø, Norway.

* cited by examiner

*Primary Examiner*—Robert B. Mondesi
(74) *Attorney, Agent, or Firm*—Buchanan Ingersoll & Rooney PC

(57) ABSTRACT

The present invention relates to a method for prevention or reduction of scar tissue and/or adhesion formation wherein a therapeutically effective amount of a substance that inhibits a pro-inflammatory cytokine such as TNF or IL-1, is administered to a patient in need of said treatment.

10 Claims, No Drawings

USE OF CYTOKINE INHIBITORS

CROSS-REFERENCE TO RELATED APPLICATION

This application claims priority under 35 U.S.C. §§ 119 and/or 365 to Swedish Patent Application Serial No. 0200667-4 entitled "Novel Use of Cytokine Inhibitors" and filed on Mar. 5, 2002, the entire content of which is hereby incorporated by reference in its entirety.

FIELD OF THE INVENTION

The present invention relates to pharmaceutical compositions and methods for prevention and/or reduction of formation of scar tissue and/or formation of adhesions.

BACKGROUND OF THE INVENTION

In general, wound healing is a positive physiological reaction that may restore anatomy and function of various tissues after trauma. The trauma may be accidental, the result of surgical intervention or the effect of a disease or genetic condition. The ideal end result of wound healing should be to restore the tissues to the situation before the trauma. One important part of the wound healing process is to form connective tissues or scar tissue that may support the healing tissues during wound healing and regeneration. However, in many cases during wound healing, the newly formed connective tissues (scar tissue) may interfere negatively with the normal function of the healing tissues. The wound healing with formation of new connective tissues may also induce adhesions that may induce pathological conditions per se. Adhesions and scarring may also reduce the possibilities of later surgical intervention of the injured tissue if needed. Scar tissue may also induce cosmetically undesirable results such as cheloid formation. Examples of adhesions and scarring may be found virtually in any organ or tissue undergoing wound healing after trauma or surgery. Following abdominal surgery and following gynecological surgery it is not uncommon that the surgical procedure per se may induce adhesions that may both make later surgery more difficult and even induce pathological conditions such as ileus. Following spinal surgery it is common to have a situation with a dense scar formation called epidural fibrosis. This may in certain case induce significant difficulties for repeated surgery and has also been suggested to induce compression of the adjacent nerve tissue. In other organs excessive wound healing may induce unwanted fixation of tissues and structures that may reduce function and induce pathological conditions. In general, a method for controlling the wound healing, particularly the formation of scar tissue and adhesions, would be of a great value in most cases of posttraumatic or post surgical wound healing.

In the literature it is has been recognized that foetal tissues heal with emphasis of regeneration of the injured tissue with no or little scar formation. In contrast, adult tissues instead may result in scar formation that may dominate over tissue regeneration. The fibroblasts that invade the area of wound healing have been suggested to play a key role in scar formation since they are the cells that are responsible for the formation of collagen, which is the main constituent of a scar. The fibroblasts should also play a key role in adhesion formation since the main component of adhesions is collagen formed by fibroblasts.

Since the fibroblasts are responsible for producing collagen attention has been drawn to the regulation of the fibroblasts in order to reduce scar formation. Transforming growth factor (TGF), which is an anti-inflammatory cytokine, and fibroblast growth factor (FGF) are known to stimulate the fibroblasts to produce collagen. Attempts have been made to administer a TGF-inhibitor for this purpose with varying degree of success. Tumor necrosis factor alpha (TNF) and interleukin 1 (IL-1) may reduce collagen production from fibroblasts in in vitro systems. However, no attempts have been made to reduce scar formation by administration of these two cytokines.

SUMMARY OF THE INVENTION

Based on the knowledge derived from the literature the inventor assessed the efficacy of inhibiting scar formation by administration of TNF in a laminectomy model on the rat (see the Comparative Example below). To his surprise, he found, contrary to what could be expected, that the wound healing was significantly impaired in the rats exposed to TNF. Scar formation and adhesions were also more common after administration of TNF compared to control.

Since administration of TNF increased scar formation and also negatively influenced the wound healing per se, the inventor realized that the in vitro data acquired in experimental settings regarding fibroblast regulation are not applicable in vivo, and that these findings had to be re-evaluated in light of the in vivo situation.

The cytokine network is complex and what may seem to be evident from an in vitro setting may often prove not to be applicable in the in vivo setting. The in vivo situation at the area of wound healing comprises a vast number of known and unknown substances that may interact in ways not present in vitro. Administration of a cytokine in one concentration may have an effect that is counteracted by administration of the same cytokine in a higher dose due to synergistic inhibition and stimulation between the various cytokines as well as physiological inhibition of its release from adjacent cells.

One key mechanism essential for the formation of a scar is the physiological, inflammatory process that occurs early at the location of wound healing. The inflammation induces an increased blood flow in the wound healing area. The inflammation also induces an activation of adhesion molecules that, together with a simultaneous increase in vascular permeability, may facilitate the migration of inflammatory cells to the wound healing site. Inflammatory mediators also have leucotactic or chemotactic properties, i.e. attract white blood cells to the area of wound healing. Two important inflammatory mediators responsible for this leucotaxis are TNF and IL-1. In delayed type hypersensitivity (DTH), TNF and IL-1 augment the inflammatory reaction induced by inflammatory cells. TNF and IL-1 synergistically with other chemokines stimulate local macrophages to produce fibroblast stimulating substances that will stimulate the fibroblasts to produce collagen.

The inventor therefore assumed that a more feasible way to prevent scar formation than previously suggested was to reduce the activity of the involved substances, which he also later found to be true. This both prevent cell migration to the site of wound healing and also reduces the production of fibroblast stimulating substances. Since TNF and IL-1 are responsible for both these mechanisms, the most efficient way to reduce scar formation and adhesion is to inhibit the action of these two pro-inflammatory cytokines or other pro-inflammatory cytokines.

The characterizing features of the invention will be evident from the following description and the appended claims.

DETAILED DESCRIPTION OF THE INVENTION

As discussed above, and further demonstrated in the Example below wherein administration of infliximab to rats with a standardized laminectomy is discussed, the inventor found, contrary to what could be expected from existing literature, that inhibition of pro-inflammatory cytokines is an efficient way to control wound healing and to prevent and/or reduce scar tissue formation and/or adhesion formation. Such pro-inflammatory cytokines are tumor necrosis factor (TNF), interleukin 1 (IL-1), interleukin 6 (IL-6), interleukin 8 (IL-8), interleukin 12 (IL-12), interleukin 15 (IL-15), interleukin 17 (IL-17), interleukin 18 (IL-1), granulocytes-macrophage colony stimulating factor (GM-CSF), macrophage colony stimulating factor (M-CSF), monocyte chemotactic protein-1 (MCP-1), macrophage inflammatory protein 1 (MIP-1), RANTES (regulated upon activation, normal T-cell expressed, and presumably secreted), epithelial cell-derived neutrophil attractant-78 (ENA-78), oncostatin-M (OSM), fibroblast growth factor (FGF), platelet derived growth factor (PDGF), and vascular endothelial growth factor (VEGF); and in particular TNF (also called TNF-$\alpha$) and IL-1 (including both IL-1$\alpha$ and IL-1$\beta$). The exact mechanisms behind this are not fully known. However, the reduced scar formation may be the result of a reduced inflammatory reaction at the wound site, with reduced recruitment of inflammatory cells and fibroblasts, and by a reduced stimulation of macrophages.

The use and method according to the invention for reduction of scar formation under these conditions are extremely valuable for controlling wound healing, thereby maintaining the normal function and regeneration of the injured tissue, allowing for repeated surgery and reducing the risk of scar induces pathological conditions. The pharmaceutical composition and method according to the invention are thus suitable for treatment of posttraumatic tissue injury. Posttraumatic tissue injury may be, for example, the result of an accident. Posttraumatic tissue injury may also be caused by surgery or surgical intervention. Scar formation may also result from a pathological condition. The pathological condition may be caused by a vascular disease, such as bleeding or infarct, which may lead to necrosis. The pathological condition may also be caused by a toxic influence, such as damage caused by an acid, or by thermic injury, such as burn injury. Furthermore, the pathological condition may be of a genetic origin, such as cystic fibrosis. The end result of wound healing may also produce hypertrophic scarring, e.g. cheloid.

The suggested treatment is applicable at all kinds of surgery. It may also be used after traumatic tissue injury. Tissue injury may also be the result of toxic influence, as the result of reduced blood flow due to vascular disease, or as the result of a thermic injury, and the treatment according to the invention is applicable also for these three latter conditions. The invention is also applicable to prevent cheloid formation.

For the purpose of this disclosure, the terms "blocking agent", "blocking substance", "inhibitor" and "antagonist" may be used interchangeably.

As stated above, inhibition of a pro-inflammatory cytokine is useful for the reduction of scar formation. This inhibition is possible to achieve by any suitable cytokine inhibitor, such as available pharmacological compositions.

Persons skilled in the art are well aware of what is intended by a pro-inflammatory cytokine. For the purpose of this disclosure, it may, however, be further clarified that the expression "a pro-inflammatory cytokine" relates to any substance from the cytokine family that posses one or more of the following specific mechanisms of action: 1) increasing vascular permeability, 2) attracting white blood cells (leucotaxia or chemotaxia), 3) activating macrophages, and 4) recruiting macrophages to the site of wound healing. These effects may be assessed for each individual substance by use of the assays disclosed below. "A substance that inhibits a pro-inflammatory cytokine" as it is used herein thus relates to a substance that may block one or more of the four listed effects in the assays disclosed below. However, due to differences between species, one may also translate findings from the experimental setting to the human situation. For instance, if a monoclonal antibody with specificity towards a specific cytokine of a certain species inhibits the action of the cytokine in one of the three ways disclosed below in that specific species, one may assume that a monoclonal antibody, with specificity towards the human version of the cytokine, may inhibit this cytokine in the human situation.

1) Assay for increase of vascular permeability: A golden hamster, weighing 65-100 g, is anaesthetized with a mixture of Apozepam® (Diazepam 5 mg/ml Apothekarnes Laboratorium, Oslo, Norway) and Mebumal Vet® (Penthobarbital 60 mg/ml, NordVacc Vaccin AB, Malmö, Sweden) volume ratio 10:1. An initial dose of 0.3 ml is given intraperitoneally. Additional injections of 0.1-0.4 ml are administered each 30 minutes. The hamster is placed on a heated (37° C.) perspex plate, and the right cheek-pouch is everted over a translucent rubber plate and covered with plastic film in order to prevent reduction in blood flow rate due to direct exchange of oxygen. An injection of 0.3 ml of FITC-Dextran (mw 150,000, 25 mg/ml, Sigma, St Louis, USA) is made in the femoral vein for fluorescence vital microscopic observations of macromolecular extravascular leakage. Temperature and humidity is controlled by irrigation of saline at 37° C. An injection of approximately 0.02 ml of a suitable concentration of the substance to be tested is made between the two layers of the cheek-pouch using a thin injection needle (diameter 0.4 mm). The same volume of saline is performed in an adjacent part of the cheek-pouch at a distance from the other injection site sufficient to eliminate the risk of communication between the saline and the tested substance within the cheek-pouch. The injection procedures are carried out under a stereomicroscope to minimize mechanical damage to the microvessels. Microvascular reactions are studied for 60 minutes at various magnifications, using fluorescence microscopic techniques (Leitz, Wetzlar, Germany). A pro-inflammatory cytokine as defined according to the present invention induces a leakage of the fluorescent macromolecule FITC-dextran. A similar leakage should not be observed at the site injected by saline.

2) Assay for leucotaxia or chemotaxia: A pig, bodyweight 25-30 kg, is anaesthetized with an intramuscular injection of 20 mg/kg bodyweight of Ketalar® (ketamine 50 mg/ml, Parke-Davis, Morris Plains, N.J.) and an intravenous injection of 4 mg/kg bodyweight of Hypnodil® (methomidate chloride 50 mg/ml, AB Leo, Helsingborg, Sweden) and 0.1 mg/kg bodyweight of Stresnil® (azaperon, 2 mg/ml, Janssen Pharmaceutica, Beerse, Belgium). Anaesthesia is maintained by additional intravenous injections of 2 mg/kg bodyweight of Hypnodil® and 0.05 mg/kg bodyweight of Stresnil®. One ml of a fluid containing a sufficient concentration of the substance to be tested is placed, in a suitable concentration locally in its natural form, in slow-release preparations or by continuous administration by osmotic mini-pumps, in a specially designed titanium-chamber. The chamber is 5 mm high and has a diameter of 15 mm. The top could be dismounted and is perforated with 18 holes, each with a diameter of 1.4 mm. The chamber, together with one chamber with the same volume of saline, are placed subcutaneously in the lumbar region through separate incisions, with no communication between the chambers. After 7 days the pig is reanaesthetized similar to the first procedure. The chambers are harvested and the content of the chamber is placed in a test-tube together with 1 ml of Hanks' Balanced Salt Solution (Life Technologies, Paisley, Scotland). From this suspension, 100 µl is used to wash out the chamber for remaining cells. This procedure is repeated 5 times. The test-tube is then shaken for 15 seconds. A total of 25 µl of the suspension and 25 µl of Türk's staining medium (Sigma, St Louis, USA) are mixed and placed in a chamber of Bürker. The total number of leukocytes in each chamber is determined using light microscopy. The chamber with a pro-inflammatory cytokine as defined according to the present invention then contains significantly more white blood cells than the chamber with only saline.

3) Assay for activation of macrophages: A macrophage cell line is bought and cultured according to the description of the manufacturer. Examples of other cell lines which can be used are: DH-82 from ECACC, Salisbury, Wiltshire, Great Britain; ACC288, ACC269 or ACC416 from Deutsche Sammlung von Mikroorganismen un Zellkulturen GmbH (DSMZ); or ICLC ATL98011 from Institute of Pharmacological Sciences, Milan Italy. The cells are cultured in multiple-well culture plates. The substance to be tested is applied to the culture-wells in various concentrations. After incubation for 6-72 hours, aliquots of the culture media (25-50 µl) of the culture media are used for assays. Assays of TNF and IL-8 and nitric oxide (NO) are performed using commercially available assays and the results are compared with assays from culture media without the addition of the substance to be tested. A pro-inflammatory cytokine as defined according to the present invention induces significantly higher levels of one or more of TNF, IL-8 or NO in the culture media compared to culture media without the tested substance.

4) Assay for recruitment of macrophages to the site of wound healing: Rats are anaesthetized with a standardized combination of pentobarbital and diazepam. The skin on the back is shaved. A 3 cm long midline incision is made in the skin and in the underlying muscle. The substance to be tested is applied in a suitable concentration locally in its natural form, in slow-release preparations or by continuous administration by osmotic mini-pumps. In control experiments, the same amount and administration of saline is executed. The skin is sutured. After 1-4 weeks the rat is re-anaesthetized and the area of wound healing in the skin and in the muscle is harvested and processed for immunohistochemistry. Commercially available antibodies for macrophage specific CD-molecules (e.g., CDw17, CD23, CD25, CD26, CD64, CD68, CD69, CD71, CD74, CD 80, CD88, CD91 and CD105) are used to visualize the presence of macrophages in the healing tissues. The number of macrophages is then found to be significantly higher in the healing tissue when exposed to the tested substance than in tissues exposed to saline control.

Inhibition of pro-inflammatory cytokines: An inhibitor of a pro-inflammatory cytokine as defined according to the present invention will reduce the effects of the pro-inflammatory cytokine in one or more of the four assays above, i.e. increase of vascular permeability, leucotaxia and activation or recruitment of macrophages, and/or it will have an inhibitory effect on the recruitment of macrophages in the assay for inhibition of recruitment of macrophages disclosed below.

5) Assay for inhibition of recruitment of macrophages to site of wound healing: Rats are anaesthetized with a standardized combination of pentobarbital and diazepam. The skin on the back is shaved. A 3 cm long midline incision is made in the skin and in the underlying muscle. The skin is sutured. The animal receives treatment by a cytokine inhibitor in a suitable concentration and form of administration. Control animals receive no treatment. After 1-4 weeks the rat is re-anaesthetized and the area of wound healing in the skin and in the muscle is harvested and processed for immunohistochemistry. Commercially available antibodies for macrophage specific CD-molecules (e.g. CDw17, CD23, CD25, CD26, CD64, CD68, CD69, CD71, CD74, CD 80, CD88, CD91 and CD105) are used to visualize the presence of macrophages in the healing tissues. The number of macrophages is then found to be significantly lower in the healing tissue after treatment with the cytokine inhibitor than in control animals.

The term "patient", as it is used herein, relates to any human or non-human mammal in need of treatment according to the invention.

The scar formation that may be prevented according to the present invention is formation of any kind of scar, such as scars caused by surgery, e.g. repeated surgery, and scars caused by traumatic tissue injury, tissue injury resulting from toxic influence, or thermic injury, or as the result of reduced blood flow due to vascular disease.

The term "treatment" used herein relates to both treatment in order to cure or alleviate a disease or a condition, and to treatment in order to prevent the development of a disease or a condition. The treatment may either be performed in an acute or in a chronic way.

There are several different types of inhibitors of pro-inflammatory cytokines that may be used according to the invention:

Specific TNF blocking substances, such as
Monoclonal antibodies, e.g. infliximab, CDP-571 (Humicader™), D2E7, and CDP-870,
Soluble cytokine receptors, e.g. etanercept, lenercept, pegylated TNF-receptor type I, TBP-1
TNF-receptor antagonists
Antisense oligonucleotides, e.g. ISIS-104838,
Non-specific TNF blocking substances, such as:
MMP inhibitors (i.e. matrix metalloproteinase inhibitors, or TACE-inhibitors, i.e., TNF-α Converting Enzyme-inhibitors)
  Tetracyclines, for example Doxycycline, Lymecycline, Oxitetracycline, Tetracycline, Minocycline and synthetic tetracycline derivatives, such as CMT, i.e., chemically modified tetracyclines,
  Prinomastat (AG3340)
  Batimastat
  Marimastat
  KB-R7785
  TIMP-1, TIMP-2, adTIMP-1 (adenoviral delivery of TIMP-1), adTIMP-2 (adenoviral delivery of TIMP-2)
Quinolones, for example Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin and Temafloxacin
Thalidomide derivates, e.g. SelCID (i.e. Selective Cytokin inhibitors), CC-1088, CDC-501, CDC-801, and Linomide (Roquininex®)
Lazaroids, e.g., non-glucocorticoid 21-aminosteroids such as U-74389G (16-desmethyl tirilazad) and U-74500
Prostaglandins; iloprost (prostacyclin)
Cyclosporin
Pentoxifyllin derivates
Hydroxamic acid derivates
Napthopyrans
Phosphodiesterase I, II, III, IV, and V-inhibitors, e.g., CC-1088, Ro 20-1724, rolipram, amrinone, pimobendan, vesnarinone, SB 207499 (Ariflo®)
Melancortin agonists, e.g., HP-228
Other TNF blocking substances, such as:

Lactoferrin, and peptides derived from lactoferrin such as those disclosed in U.S. Pat. No. 7,253,143 B1, the disclosure of which is hereby incorporated by reference.

CT3
ITF-2357
PD-168787
CLX-1100
M-PGA
NCS-700
PMS-601
RDP-58
TNF-484A
PCM-4
CBP-1011
SR-31747
AGT-1
Solimastat
CH-3697
NR58-3.14.3
RIP-3
Sch-23863
Yissum project no. 11649
Pharma project nos. 6181, 6019 and 4657
SH-636
Specific IL-1α and IL-1β blocking substances, such as:
Monoclonal antibodies
Soluble cytokine receptors
IL-1 type II receptor (decoy RII)
Receptor antagonists; IL-1ra, (Orthogen®, Orthokin®)
Antisense oligonucleotides
Non-specific IL-1α and IL-1β blocking substances, such as
  MMP inhibitors (i.e. matrix metalloproteinase inhibitors),
    Tetracyclines, for example Doxycycline, Trovafloxacin, Lymecycline, Oxitetracycline, Tetracycline, Minocycline, and synthetic tetracycline derivatives, such as CMT, i.e. chemically modified tetracyclines;
    Prinomastat (AG3340)
    Batimastat
    Marimastat
    KB-R7785
    TIMP-1, TIMP-2, adTIMP-1, adTIMP-2
  Quinolones (chinolones), for example Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin;
Prostaglandins; Iloprost (prostacyclin);
Phosphodiesterase I, II, III, IV, and V-inhibitors; CC-1088, Ro 20-1724, rolipram, amrinone, pimobendan, vesnarinone, SB 207499.
Specific IL-6 blocking substances, such as:
Monoclonal antibodies
Soluble cytokine receptors
Receptor antagonists
Antisense oligonucleotides
Non-specific IL-6 blocking substances, such as:
MMP inhibitors (i.e. matrix metalloproteinase inhibitors)
  Tetracyclines, for example Doxycycline, Lymecycline, Oxitetracycline, Tetracycline, Minocycline, and synthetic tetracycline derivatives, such as CMT, i.e. chemically modified tetracyclines;
  Prinomastat (AG3340)
  Batimastat
  Marimastat
  KB-R7785
  TIMP-1, TIMP-2, adTIMP-1, adTIMP-2
Quinolones (chinolones), for example Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin,
Prostaglandins; Iloprost (prostacyclin)
Cyclosporin
Pentoxifyllin derivates
Hydroxamic acid derivates
Phosphodiesterase 1, II, III, IV, and V-inhibitors; CC-11088, Ro 20-1724, rolipram, amrinone, pimobendan, vesnarinone, SB 207499
Melanin and melancortin agonists; HP-228
Specific IL-8 blocking substances, such as:
Monoclonal antibodies
Soluble cytokine receptors
Receptor antagonists
Antisense oligonucleotides
Non-specific IL-8 blocking substances, such as:
  Quinolones (chinolones), for example Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin,
Thalidomide derivates, e.g. SelCID (i.e. Selective Cytokin inhibitors), such as; CC-1088, CDC-501, CDC-801 and Linomide (Roquininex®)
Lazaroids
Cyclosporin
Pentoxifyllin derivates.

The pharmaceutical composition according to the invention may also comprise other substances, such as an inert vehicle, or pharmaceutical acceptable adjuvants, carriers, preservatives etc., which are well known to persons skilled in the art.

The administration of the TNF-inhibitor and/or IL-1 inhibitor and/or pharmaceutical composition according to the invention should preferably be performed early after injury to limit the inflammatory reaction occurring at the wound healing site. The TNF-inhibitor and/or IL-1 inhibitor and/or pharmaceutical composition according to the invention is administered once or repeatedly until the desired result is obtained. The TNF-inhibitor and/or IL-1 inhibitor and/or pharmaceutical composition according to the invention is administered in a therapeutically effective amount, i.e. an amount that will lead to the desired therapeutical effect and thus lead to an improvement of the patient's condition.

The TNF-inhibitor and/or IL-1 inhibitor and/or pharmaceutical composition according to the invention may be administered in any efficacious way normally used to administer such substances. Thus, the administration may be done both systemically and locally and may be performed before, during and/or after all kind of surgical or traumatic tissue injury. The suggested treatment may also be applicable at tissue injury as the result of pathological conditions including vascular disease and toxic influence. The TNF-inhibitor and/or IL-1 inhibitor and/or pharmaceutical composition according to the invention may for example be injected via intraarticular, intravenous (i.v.), intramuscular (i.m.), intraperitoneal (i.p.), intrathecal (i.t.), epidural, intracerebroventricular (i.c.v.) or subcutaneous (s.c.) routes by bolus injections or by continuous infusion. They may also be administered orally (per os), e.g. in the form of oral preparations, such as pills, syrups, or lozenges. Furthermore, they may be administered by inhalation or intranasally. Moreover, they may be administered transepidermally, e.g. in the form of topical preparations such as lotions, gels, sprays, ointments or patches. They may also be administered in an irrigation solution or by localized injection. Finally, they may also be administered by genetical engineering.

According to one preferred embodiment of the invention, the pharmaceutical composition is formulated as a sustained-release preparation. The substance according to the invention may then, for example, be encapsulated in a slowly-dissolving biocompatible polymer.

Examples of suitable doses for different administration routes are given below. Additional dosages would be apparent to the artisan of ordinary skill. The provided dosages include any range in between as can be determined on a case-by-case basis.

| | | |
|---|---|---|
| Per os | 10-300 mg | |
| i.m. | 25-100 mg | |
| i.v. | 2.5-25 mg | |
| i.t. | 0.1-25 mg | daily to every 3rd month |
| inhalation | 0.2-40 mg | |
| transepidermally | 10-100 mg | |
| intranasally | 0.1-10 mg | |
| s.c. | 5-10 mg | |
| i.c.v. | 0.1-25 mg | daily to every 3rd month |
| epidurally | 1-100 mg | |

Examples of suitable doses for different TNF inhibitors are given below.

| Drug | Preferred Dosage | More Preferred Dosage | Most Preferred Dosage |
|---|---|---|---|
| Lenercept | | | |
| i.v. | 5-200 | 10-100 | 30-80 |
| (all doses given in mg for administration once every 4th week) | | | |
| TBP-1 | | | |
| i.v. | 5-200 | 10-100 | 30-80 |
| (all doses given in mg for administration once every 4th week) | | | |
| CDP-571 | | | |
| Humicade ® | | | |
| i.v. | 1-100 | 5-10 | 5-10 |
| (all doses given in mg/kg body weight for administration as a single dose) | | | |
| D2E7 | | | |
| i.v. | 0.1-50 | 0.5-10 | 1-10 |
| s.c. | 0.1-50 | 0.5-10 | 1-10 |
| (all doses given in mg/kg body weight for administration as a single dose | | | |
| Iloprost | | | |
| i.v. | 0.1-2000 | 1-1500 | 100-1000 |
| (all doses given in μg/kg body weight/day) | | | |
| intranasally | 50-250 | 100-150 | 100-150 |
| (all doses given in μg/day) | | | |
| CC-1088 | | | |
| Per os | 50-1200 | 200-800 | 400-600 |
| (all doses given in mg/day) | | | |
| CDP-870 | | | |
| i.v. | 1-50 | 2-10 | 3-8 |
| (all doses given in mg/kg body weight for administration once every 4th week) | | | |
| s.c. | 50-600 | 100-400 | 100-200 |
| (all doses given in mg/day) | | | |
| Linomide | | | |
| Roquinimex ® | | | |
| Per os | 0.1-25 | 5-20 | 10-15 |
| (all doses given in mg/kg body weight/day) | | | |

| Drug | Preferred Dosage | More Preferred Dosage | Most Preferred Dosage |
|---|---|---|---|
| HP-228 | | | |
| i.v. | 5-100 | 10-50 | 20-40 |
| (all doses given in μg/kg body weight) | | | |
| ISIS-104838 | | | |
| Per os | 1-100 | 10-50 | 20-50 |
| s.c. | 1-100 | 10-50 | 20-50 |
| i.v. | 1-100 | 10-50 | 20-50 |
| (all doses given in mg) | | | |
| Ariflo ® | | | |
| SB 207499 | | | |
| Per os | 10-100 | 30-60 | 30-45 |
| (all doses given in mg/day) | | | |
| KB-R7785 | | | |
| s.c. | 100-500 | 100-300 | 100-250 |
| (all doses given in mg/kg body weight/day) | | | |
| Prinomastat (AG3340) | | | |
| Per os | 1-250 | 5-100 | 10-50 |
| (all doses given in mg for administration twice daily) | | | |
| Batimastat | | | |
| Per os | 1-250 | 5-100 | 10-50 |
| (all doses given in mg for administration twice daily) | | | |
| Marimastat | | | |
| Per os | 1-250 | 5-100 | 10-50 |
| (all doses given in mg for administration twice daily) | | | |
| CDC-501 | | | |
| Per os | 50-1200 | 200-800 | 400-600 |
| (all doses given in mg/day) | | | |
| CDC-801 | | | |
| Per os | 50-1200 | 200-800 | 400-600 |
| (all doses given in mg/day) | | | |

It is possible to use either one or two or more substances according to the invention in the prevention of scar formation. When two or more substances are used they may be administered either simultaneously or separately.

The substances according to the invention may also be administered in combination with other drugs or compounds, provided that these other drugs or compounds do not eliminate the effects desired according to the present invention, i.e. the effect on TNF.

It is understood that the response by individual patients to the substances according to the invention or combination therapies, may vary, and the most efficacious combination of drugs for each patient will be determined by the physician in charge.

The invention is further illustrated in the Example below, which is only intended to illustrate the invention and should in no way be considered to limit the scope of the invention. The invention is also compared to the stated of the art in the Comparative Example.

EXAMPLE

Four rats were anaesthetized with a standardized combination of pentobarbital and diazepam. The skin on the back was shaved. Through a midline incision, a laminectomy of the 4th lumbar vertebra was performed. The spinal muscles and the skin was sutured. Two rats received an intraperitoneal injection of 4 mg/kg of infliximab. Infliximab is a monoclonal antibody towards TNF with an inhibiting action with a duration of 1-2 months following single administration in the dosage used. The other two rats received an intraperitoneal injection of saline. After 2 weeks, the rats were reanaesthesized and wound healing and scar formation were evaluated by a person being unaware of the experimental protocol. Wound healing was considered normal in both groups. In the group of animals that received infliximab, the previous location of the lamina was filled with soft connective tissue that did not adhere to the spinal dura mater and was easy to remove. In the non-treated group, there was a somewhat more dense lump of connective tissue that was adherent to the spinal dura mater.

Comparative Example (Not According to the Invention)

Following a laminectomy of the lamina of the 4th lumbar vertebra either 0.15 ml of 20 ng/ml of recombinant rat TNF in distilled water or just 0.15 ml of distilled water was instilled in the laminectomy space. The wound was sutured and assessed after 1 week, 2 weeks regarding wound healing and scar tissue formation. There were 20 rats in total. Five rats were treated with TNF and five rats with only distilled water for each duration. Contrary to what could be expected the wound healing was significantly impaired in the rats exposed to TNF. The scar formation in the laminectomy space was significantly more pronounced in the TNF exposed rats, also contrary to what could be expected from the literature. The scar in the TNF exposed rats was also attached to the dura mater covering the spinal cord by adhesions. All observations were performed in a blinded fashion.

What is claimed is:

1. A method for reduction of adhesion formation comprising administering a therapeutically effective amount of a substance that inhibits a pro-inflammatory cytokine to a patient in need thereof, wherein; the administration of the substance that inhibits a pro-inflammatory cytokine causes a reduction in adhesion formation, and wherein; said substance is the peptide of SEQ ID NO: 3 or SEQ ID NO: 37.

2. The method of claim 1, for treatment of post-traumatic tissue injury.

3. The method of claim 1, for treatment of a thermic injury.

4. The method of claim 1, for treatment of a pathological condition with scar formation.

5. The method of claim 2, wherein said post-traumatic tissue injury is caused by surgery.

6. The method of claim 4, wherein said pathological condition with scar formation is caused by a vascular disease selected from the group consisting of bleeding and infarct.

7. The method of claim 4, wherein said pathological condition with scar formation is caused by a toxic influence.

8. The method of claim 4, wherein said pathological condition with scar formation is caused by cystic fibrosis.

9. The method of claim 1, wherein said substance is locally administered.

10. The method of claim 1, wherein said substance is systemically administered.

* * * * *

```
SEQUENCE LISTING

<160> NUMBER OF SEQ ID NOS: 102

<210> SEQ ID NO 1
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: PEPTIDE
<222> LOCATION: (1)
<223> OTHER INFORMATION: Amino acid 1 is Xaa wherein Xaa = Glu or no
      amino acid.
<220> FEATURE:
<221> NAME/KEY: PEPTIDE
<222> LOCATION: (2)
<223> OTHER INFORMATION: Amino acid 2 is Xaa wherein Xaa = Ala or no
      amino acid.
<220> FEATURE:
<221> NAME/KEY: PEPTIDE
<222> LOCATION: (5)
<223> OTHER INFORMATION: Amino acid 5 is Xaa wherein Xaa = Cys or Ala.
<220> FEATURE:
<221> NAME/KEY: PEPTIDE
<222> LOCATION: (7)
<223> OTHER INFORMATION: Amino acid 7 is Xaa wherein Xaa = Gln or Lys.
<220> FEATURE:
<221> NAME/KEY: PEPTIDE
<222> LOCATION: (11)
<223> OTHER INFORMATION: Amino acid 11 is Xaa wherein Xaa = Asn or Asp.
<220> FEATURE:
<221> NAME/KEY: PEPTIDE
<222> LOCATION: (17)..(25)
<223> OTHER INFORMATION: Amino acids 17 25 are Xaa wherein Xaa = Gly,
      Pro, Pro, Val, Ser, Cys, Ile, Lys, Arg
<220> FEATURE:
<221> NAME/KEY: MOD_RES
<222> LOCATION: (25)
<223> OTHER INFORMATION: AMIDATION
<220> FEATURE:
<223> OTHER INFORMATION: Description of Artificial Sequence: of natural
      or artificial origin, corresponding to modification of the
      sequence consisting of aa 16 40 in human lactoferrin
```

```
<400> SEQUENCE: 1

Xaa Xaa Thr Lys Xaa Phe Xaa Trp Gln Arg Xaa Met Arg Lys Val Arg
1               5                   10                  15

Xaa Xaa Xaa Xaa Xaa Xaa Xaa Xaa Xaa
            20                  25

<210> SEQ ID NO 2
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION
<220> FEATURE:
<223> OTHER INFORMATION: Description of Artificial Sequence: of natural
      or artificial origin, corresponding to a modification of the
      sequence consisting of amino acids 16 40 in human lactoferrin

<400> SEQUENCE: 2

Glu Ala Thr Lys Cys Phe Gln Trp Gln Arg Asn Met Arg Lys Val Arg
1               5                   10                  15

Gly Pro Pro Val Ser Cys Ile Lys Arg
            20                  25

<210> SEQ ID NO 3
<211> LENGTH: 25
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION
<220> FEATURE:
<221> NAME/KEY: DISULFID
<222> LOCATION: (5)..(22)
<220> FEATURE:
<223> OTHER INFORMATION: Description of Artificial Sequence: of natural
      or artificial origin, corresponding to a modification of the
      sequence consisting of amino acids 16 40 in human lactoferrin

<400> SEQUENCE: 3

Glu Ala Thr Lys Cys Phe Gln Trp Gln Arg Asn Met Arg Lys Val Arg
1               5                   10                  15

Gly Pro Pro Val Ser Cys Ile Lys Arg
            20                  25

<210> SEQ ID NO 4
<211> LENGTH: 23
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (23)..(23)
<223> OTHER INFORMATION: AMIDATION
<220> FEATURE:
<223> OTHER INFORMATION: Description of Artificial Sequence: of natural
      or artificial origin, corresponding to a modification
``` of the sequence consisting of amino acids 18 40 in
human lactoferrin

<400> SEQUENCE: 4

Thr Lys Cys Phe Gln Trp Gln Arg Asn Met Arg Lys Val Arg Gly Pro
1               5                   10                  15

Pro Val Ser Cys Ile Lys Arg
            20

<210> SEQ ID NO 5
<211> LENGTH: 23
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (23)
<223> OTHER INFORMATION: AMIDATION
<220> FEATURE:
<221> NAME/KEY: DISULFID
<222> LOCATION: (3)..(20)
<220> FEATURE:
<223> OTHER INFORMATION: Description of Artificial Sequence: of natural
      or artificial origin, corresponding to a modification
      of the sequence consisting of amino acids 18 40 in
      human lactoferrin

<400> SEQUENCE: 5

Thr Lys Cys Phe Gln Trp Gln Arg Asn Met Arg Lys Val Arg Gly Pro
1               5                   10                  15

Pro Val Ser Cys Ile Lys Arg
            20

<210> SEQ ID NO 6
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<223> OTHER INFORMATION: Description of Artificial Sequence: of natural
      or artificial origin, corresponding to a modification
      of the sequence consisting of amino acids 18 31 in
      human lactoferrin

<400> SEQUENCE: 6

Thr Lys Ala Phe Lys Trp Gln Arg Asp Met Arg Lys Val Arg
1               5                   10

<210> SEQ ID NO 7
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:

```
<221> NAME/KEY: BINDING
<222> LOCATION: (5)..(9)
<223> OTHER INFORMATION: LACTAM
<220> FEATURE:
<223> OTHER INFORMATION: Description of Artificial Sequence: of natural
      or artificial origin, corresponding to a modification
      of the sequence consisting of aa 18 31 in human
      lactoferrin; a lactam is formed between aa 5 and 9

<400> SEQUENCE: 7

Thr Lys Ala Phe Lys Trp Gln Arg Asp Met Arg Lys Val Arg
 1               5                  10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 12 31 of the protein
      human lactoferrin

<400> SEQUENCE: 8

Val Ser Gln Pro Glu Ala Thr Lys Cys Phe Gln Trp Gln Arg Asn Met
 1               5                  10                  15

Arg Lys Val Arg
            20

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 12 18 of the protein
      human lactoferrin

<400> SEQUENCE: 9

Val Ser Gln Pro Glu Ala Thr
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 13 19 of the protein
      human lactoferrin

<400> SEQUENCE: 10

Ser Gln Pro Glu Ala Thr Lys
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 14 20 of the protein
      human lactoferrin

<400> SEQUENCE: 11

Gln Pro Glu Ala Thr Lys Cys
```

-continued

```
   1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 15 21 of the protein
      human lactoferrin

<400> SEQUENCE: 12

Pro Glu Ala Thr Lys Cys Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 22 of the protein
      human lactoferrin

<400> SEQUENCE: 13

Glu Ala Thr Lys Cys Phe Gln
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 17 23 of the protein
      human lactoferrin

<400> SEQUENCE: 14

Ala Thr Lys Cys Phe Gln Trp
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 18 24 of the protein
      human lactoferrin

<400> SEQUENCE: 15

Thr Lys Cys Phe Gln Trp Gln
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 19 25 of the protein
      human lactoferrin

<400> SEQUENCE: 16
```

```
Lys Cys Phe Gln Trp Gln Arg
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 20 26 of the protein
      human lactoferrin

<400> SEQUENCE: 17

Cys Phe Gln Trp Gln Arg Asn
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 21 27 of the protein
      human lactoferrin

<400> SEQUENCE: 18

Phe Gln Trp Gln Arg Asn Met
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 22 28 of the protein
      human lactoferrin

<400> SEQUENCE: 19

Gln Trp Gln Arg Asn Met Arg
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 23 29 of the protein
      human lactoferrin

<400> SEQUENCE: 20

Trp Gln Arg Asn Met Arg Lys
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 24 30 of the protein
      human lactoferrin

<400> SEQUENCE: 21
```

```
Gln Arg Asn Met Arg Lys Val
  1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 25 31 of the protein
      human lactoferrin

<400> SEQUENCE: 22

Arg Asn Met Arg Lys Val Arg
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 23 of the protein
      human lactoferrin

<400> SEQUENCE: 23

Glu Ala Thr Lys Cys Phe Gln Trp
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 24 of the protein
      human lactoferrin

<400> SEQUENCE: 24

Glu Ala Thr Lys Cys Phe Gln Trp Gln
  1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 25 of the protein
      human lactoferrin

<400> SEQUENCE: 25

Glu Ala Thr Lys Cys Phe Gln Trp Gln Arg
  1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 26 of the protein
      human lactoferrin
```

```
<400> SEQUENCE: 26

Glu Ala Thr Lys Cys Phe Gln Trp Gln Arg Asn
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 27 of the protein
      human lactoferrin

<400> SEQUENCE: 27

Glu Ala Thr Lys Cys Phe Gln Trp Gln Arg Asn Met
 1               5                  10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 28 of the protein
      human lactoferrin

<400> SEQUENCE: 28

Glu Ala Thr Lys Cys Phe Gln Trp Gln Arg Asn Met Arg
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 29 of the protein
      human lactoferrin

<400> SEQUENCE: 29

Glu Ala Thr Lys Cys Phe Gln Trp Gln Arg Asn Met Arg Lys
 1               5                  10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 30 of the protein
      human lactoferrin

<400> SEQUENCE: 30

Glu Ala Thr Lys Cys Phe Gln Trp Gln Arg Asn Met Arg Lys Val
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 16 31 of the protein
      human lactoferrin
```

<400> SEQUENCE: 31

Glu Ala Thr Lys Cys Phe Gln Trp Gln Arg Asn Met Arg Lys Val Arg
1               5                   10                  15

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 13 31 of the protein
      human lactoferrin

<400> SEQUENCE: 32

Ser Gln Pro Glu Ala Thr Lys Cys Phe Gln Trp Gln Arg Asn Met Arg
1               5                   10                  15

Lys Val Arg

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 14 31 of the protein
      human lactoferrin

<400> SEQUENCE: 33

Gln Pro Glu Ala Thr Lys Cys Phe Gln Trp Gln Arg Asn Met Arg Lys
1               5                   10                  15

Val Arg

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 15 31 of the protein
      human lactoferrin

<400> SEQUENCE: 34

Pro Glu Ala Thr Lys Cys Phe Gln Trp Gln Arg Asn Met Arg Lys Val
1               5                   10                  15

Arg

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 17 31 of the protein
      human lactoferrin

<400> SEQUENCE: 35

Ala Thr Lys Cys Phe Gln Trp Gln Arg Asn Met Arg Lys Val Arg
1               5                   10                  15

<210> SEQ ID NO 36
<211> LENGTH: 14

```
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 18 31 of the protein
      human lactoferrin

<400> SEQUENCE: 36

Thr Lys Cys Phe Gln Trp Gln Arg Asn Met Arg Lys Val Arg
  1               5                  10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 19 31 of the protein
      human lactoferrin

<400> SEQUENCE: 37

Lys Cys Phe Gln Trp Gln Arg Asn Met Arg Lys Val Arg
  1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 20 31 of the protein
      human lactoferrin

<400> SEQUENCE: 38

Cys Phe Gln Trp Gln Arg Asn Met Arg Lys Val Arg
  1               5                  10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 21 31 of the protein
      human lactoferrin

<400> SEQUENCE: 39

Phe Gln Trp Gln Arg Asn Met Arg Lys Val Arg
  1               5                  10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 22 31 of the protein
      human lactoferrin

<400> SEQUENCE: 40

Gln Trp Gln Arg Asn Met Arg Lys Val Arg
  1               5                  10

<210> SEQ ID NO 41
```

-continued

```
<211> LENGTH: 9
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 23 31 of the protein
      human lactoferrin

<400> SEQUENCE: 41

Trp Gln Arg Asn Met Arg Lys Val Arg
 1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Peptide of
      natural or artificial origin consisting of the
      amino acids in positions 24 31 of the protein
      human lactoferrin

<400> SEQUENCE: 42

Gln Arg Asn Met Arg Lys Val Arg
 1               5

<210> SEQ ID NO 43
<211> LENGTH: 11
<212> TYPE: PRT
<213> ORGANISM: Artificial Sequence
<220> FEATURE:
<221> NAME/KEY: PEPTIDE
<222> LOCATION: (2)..(10)
<223> OTHER INFORMATION: Amino acids 2, 4, 6 and 10 are Xaa wherein
      Xaa = Gln, Lys, Asp, Asn or Val.
<220> FEATURE:
<223> OTHER INFORMATION: Description of Artificial Sequence: of natural
      or artificial origin, corresponding to a modification
      of the sequence consisting of amino acids 21 31 in
      human lactoferrin

<400> SEQUENCE: 43

Phe Xaa Trp Xaa Arg Xaa Met Arg Lys Xaa Arg
 1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 21 31 in human
      lactoferrin

<400> SEQUENCE: 44

Phe Gln Trp Gln Arg Asn Met Arg Lys Val Arg
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 21 31 in human lactoferrin
      wherein one aa has been substituted

<400> SEQUENCE: 45
```

```
Phe Gln Trp Gln Arg Asn Met Arg Lys Val Arg
 1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 46

Cys Phe Gln Trp Gln Arg Asn Met Arg Lys Val Arg
 1               5                   10

<210> SEQ ID NO 47
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (12)
<223> OTHER INFORMATION: AMIDATION
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 47

Cys Phe Gln Trp Gln Arg Asn Met Arg Lys Val Arg
1                5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence:of natural
      or artificial origin, corresponding to the sequence
      consisting of aa 19 31 in human lactoferrin
      wherein one aa has been substituted

<400> SEQUENCE: 48

Lys Cys Phe Gln Trp Gln Arg Asn Met Arg Lys Val Arg
 1               5                   10

<210> SEQ ID NO 49
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence: of natural
      or artificial origin, corresponding to the sequence
      consisting of aa 19 31 in human lactoferrin
      wherein one aa has been modified
```

```
<400> SEQUENCE: 49

Lys Cys Phe Gln Trp Gln Arg Asn Met Arg Lys Val Arg
 1               5                  10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 18 31 in human lactoferrin
      wherein one aa has been substituted

<400> SEQUENCE: 50

Thr Lys Cys Phe Gln Trp Gln Arg Asn Met Arg Lys Val Arg
 1               5                  10

<210> SEQ ID NO 51
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<223> OTHER INFORMATION: Description of Artificial Sequence: of natural
      or artificial origin, corresponding to the sequence
      consisting of aa 18 31 in human lactoferrin
      wherein one aa has been substituted

<400> SEQUENCE: 51

Thr Lys Cys Phe Gln Trp Gln Arg Asn Met Arg Lys Val Arg
 1               5                  10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in
      human lactoferrin

<400> SEQUENCE: 52

Thr Lys Ala Phe Lys Trp Gln Arg Asp Met Arg Lys Val Arg
 1               5                  10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
```

<400> SEQUENCE: 53

Thr Lys Ala Phe Lys Trp Gln Arg Glu Met Arg Lys Val Arg
 1               5                  10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of aa 18 31 in human
      lactoferrin; a lactam is formed between aa 5 and 9
<220> FEATURE:
<221> NAME/KEY: BINDING
<222> LOCATION: (5)..(9)
<223> OTHER INFORMATION: LACTAM

<400> SEQUENCE: 54

Thr Lys Ala Phe Lys Trp Gln Arg Asp Met Arg Lys Val Arg
 1               5                  10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of aa 18 31 in human
      lactoferrin; a lactam is formed between aa 5 and 9
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<221> NAME/KEY: BINDING
<222> LOCATION: (5)..(9)
<223> OTHER INFORMATION: LACTAM

<400> SEQUENCE: 55

Thr Lys Ala Phe Lys Trp Gln Arg Glu Met Arg Lys Val Arg
 1               5                  10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in
      human lactoferrin

<400> SEQUENCE: 56

Thr Lys Lys Phe Gln Trp Gln Arg Asn Met Arg Lys Val Arg
 1               5                  10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 57

Thr Lys Lys Phe Gln Trp Gln Arg Asn Met Arg Lys Val Arg
 1               5                  10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in
      human lactoferrin

<400> SEQUENCE: 58

Thr Lys Lys Phe Gln Trp Asp Arg Lys Met Arg Lys Asp Arg
 1               5                  10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 18 31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 59

Thr Lys Lys Phe Gln Trp Asp Arg Lys Met Arg Lys Asp Arg
 1               5                  10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresp. to a modification of the seq.
      consisting of aa 18 31 in human lactoferrin; lactams formed
      between aa 3 and 7, and 9 and 13
<220> FEATURE:
<221> NAME/KEY: BINDING
<222> LOCATION: (3)..(7)
<223> OTHER INFORMATION: LACTAM
<220> FEATURE:
<221> NAME/KEY: BINDING
<222> LOCATION: (9)..(13)
<223> OTHER INFORMATION: LACTAM

<400> SEQUENCE: 60

Thr Lys Lys Phe Gln Trp Asp Arg Lys Met Arg Lys Asp Arg
 1               5                  10

```
<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresp. to a modification of the seq.
      consisting of aa 18 31 in human lactoferrin; lactams formed
      between aa 3 and 7, and 9 and 13
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION
<220> FEATURE:
<221> NAME/KEY: BINDING
<222> LOCATION: (3)..(7)
<223> OTHER INFORMATION: LACTAM
<220> FEATURE:
<221> NAME/KEY: BINDING
<222> LOCATION: (9)..(13)
<223> OTHER INFORMATION: LACTAM

<400> SEQUENCE: 61

Thr Lys Lys Phe Gln Trp Asp Arg Lys Met Arg Lys Asp Arg
 1               5                  10

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 17 31 in human
      lactoferrin

<400> SEQUENCE: 62

Ala Thr Lys Cys Phe Gln Trp Gln Arg Asn Met Arg Lys Val Arg
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 17 31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (15)
<223> OTHER INFORMATION: AMIDATION

<400> SEQUENCE: 63

Ala Thr Lys Cys Phe Gln Trp Gln Arg Asn Met Arg Lys Val Arg
 1               5                  10                  15

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: of natural
``` or artificial origin, corresponding to the sequence
consisting of amino acids 16 31 in human
lactoferrin

<400> SEQUENCE: 64

Glu Ala Thr Lys Cys Phe Gln Trp Gln Arg Asn Met Arg Lys Val Arg
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 16 31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (16)
<223> OTHER INFORMATION: AMIDATION

<400> SEQUENCE: 65

Glu Ala Thr Lys Cys Phe Gln Trp Gln Arg Asn Met Arg Lys Val Arg
1               5                   10                  15

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of amino acids 15 31 in human
      lactoferrin

<400> SEQUENCE: 66

Pro Glu Ala Thr Lys Cys Phe Gln Trp Gln Arg Asn Met Arg Lys Val
1               5                   10                  15
Arg

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: of natural
      or artificial origin, corresponding to a modification
      of the sequence consisting of amino acids 15 31 in
      human lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (17)
<223> OTHER INFORMATION: AMIDATION

<400> SEQUENCE: 67

Pro Glu Ala Thr Lys Cys Phe Gln Trp Gln Arg Asn Met Arg Lys Val
1               5                   10                  15
Arg

<210> SEQ ID NO 68

```
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 68

Ala Phe Gln Trp Gln Arg Asn Met Arg Lys Val Arg
 1               5                  10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 69

Cys Ala Gln Trp Gln Arg Asn Met Arg Lys Val Arg
 1               5                  10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 70

Cys Phe Ala Trp Gln Arg Asn Met Arg Lys Val Arg
 1               5                  10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 71

Cys Phe Gln Ala Gln Arg Asn Met Arg Lys Val Arg
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 72

Cys Phe Gln Trp Ala Arg Asn Met Arg Lys Val Arg
 1               5                  10
```

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been modified

<400> SEQUENCE: 73

Cys Phe Gln Trp Gln Ala Asn Met Arg Lys Val Arg
 1               5                  10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 74

Cys Phe Gln Trp Gln Arg Ala Met Arg Lys Val Arg
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 75

Cys Phe Gln Trp Gln Arg Asn Ala Arg Lys Val Arg
 1               5                  10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 76

Cys Phe Gln Trp Gln Arg Asn Met Ala Lys Val Arg
 1               5                  10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 77

Cys Phe Gln Trp Gln Arg Asn Met Arg Ala Val Arg
 1               5                  10

```
<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 78

Cys Phe Gln Trp Gln Arg Asn Met Arg Lys Ala Arg
 1               5                  10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 79

Cys Phe Gln Trp Gln Arg Asn Met Arg Lys Val Ala
 1               5                  10

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 80

Cys Phe Gln Leu Gln Arg Asn Met Arg Lys Val Arg
 1               5                  10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 81

Cys Phe Gln Trp Gln Lys Asn Met Arg Lys Val Arg
 1               5                  10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 82

Cys Phe Gln Trp Gln Arg Asn Leu Arg Lys Val Arg
 1               5                  10
```

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 83

Cys Phe Gln Trp Gln Arg Asn Met Lys Lys Val Arg
 1               5                  10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 84

Cys Phe Gln Trp Glu Arg Asn Met Arg Lys Val Arg
 1               5                  10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 85

Cys Phe Gln Trp Gln Glu Asn Met Arg Lys Val Arg
 1               5                  10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 86

Cys Phe Gln Trp Gln Arg Glu Met Arg Lys Val Arg
 1               5                  10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted
<220> FEATURE:
<221> NAME/KEY: MISC_FEATURE
<222> LOCATION: (5)
<223> OTHER INFORMATION: Amino acid 5 is Xaa wherein Xaa = Orn.

<400> SEQUENCE: 87

Cys Phe Gln Trp Xaa Arg Asn Met Arg Lys Val Arg
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted
<220> FEATURE:
<221> NAME/KEY: MISC_FEATURE
<222> LOCATION: (5)
<223> OTHER INFORMATION: Amino acid 5 is Xaa wherein Xaa = Nle.

<400> SEQUENCE: 88

Cys Phe Gln Trp Xaa Arg Asn Met Arg Lys Val Arg
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted
<220> FEATURE:
<221> NAME/KEY: MISC_FEATURE
<222> LOCATION: (7)
<223> OTHER INFORMATION: Amino acid 7 is Xaa wherein Xaa = Orn.

<400> SEQUENCE: 89

Cys Phe Gln Trp Gln Arg Xaa Met Arg Lys Val Arg
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted
<220> FEATURE:
<221> NAME/KEY: MISC_FEATURE
<222> LOCATION: (7)
<223> OTHER INFORMATION: Amino acid 7 is Xaa wherein Xaa = Nle.

<400> SEQUENCE: 90

Cys Phe Gln Trp Gln Arg Xaa Met Arg Lys Val Arg
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein one aa has been substituted

<400> SEQUENCE: 91

```
Cys Phe Gln Trp Lys Arg Asn Met Arg Lys Val Arg
 1               5                  10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 18 31 in human
      lactoferrin
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (12)
<223> OTHER INFORMATION: AMIDATION
<220> FEATURE:
<221> NAME/KEY: BINDING
<222> LOCATION: (5)..(9)

<400> SEQUENCE: 92

Cys Phe Gln Trp Lys Arg Asn Met Arg Lys Val Arg
 1               5                  10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein some aa have been substituted

<400> SEQUENCE: 93

Cys Phe Gln Trp Lys Arg Ala Met Arg Lys Val Arg
 1               5                  10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein some aa have been substituted

<400> SEQUENCE: 94

Cys Phe Ala Trp Lys Arg Asn Met Arg Lys Val Arg
 1               5                  10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein some aa have been substituted

<400> SEQUENCE: 95

Cys Phe Ala Trp Gln Arg Ala Met Arg Lys Val Arg
 1               5                  10
```

```
<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresponding to the sequence
      consisting of aa 20 31 in human lactoferrin
      wherein some aa have been substituted

<400> SEQUENCE: 96

Cys Phe Gln Leu Lys Lys Asn Met Lys Lys Val Arg
 1               5                  10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 20 31 in human
      lactoferrin
<220> FEATURE:
<221> NAME/KEY: BINDING
<222> LOCATION: (5)..(9)

<400> SEQUENCE: 97

Cys Phe Ala Leu Lys Lys Ala Met Lys Lys Val Arg
 1               5                  10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 18 31 in human
      lactoferrin
<220> FEATURE:
<221> NAME/KEY: BINDING
<222> LOCATION: (5)..(9)
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (14)
<223> OTHER INFORMATION: AMIDATION

<400> SEQUENCE: 98

Thr Lys Lys Phe Gln Trp Gln Arg Asn Met Arg Lys Val Arg
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: of natural
      or artificial origin, corresp. to a modification of
      the sequence consisting of aa 20 31 in human
      lactoferrin
<220> FEATURE:
<221> NAME/KEY: PEPTIDE
<222> LOCATION: (3)
<223> OTHER INFORMATION: Amino acid 3 is Xaa wherein Xaa = Gln or Ala.
<220> FEATURE:
<221> NAME/KEY: PEPTIDE
<222> LOCATION: (4)
<223> OTHER INFORMATION: Amino acid 4 is Xaa wherein Xaa = Trp or Leu.
```

```
<220> FEATURE:
<221> NAME/KEY: PEPTIDE
<222> LOCATION: (5)
<223> OTHER INFORMATION: Amino acid 5 is Xaa wherein Xaa = Gln, Lys,
      Orn, Ala or Nle.
<220> FEATURE:
<221> NAME/KEY: PEPTIDE
<222> LOCATION: (6)
<223> OTHER INFORMATION: Amino acid 6 is Xaa wherein Xaa = Arg, Lys or
      Ala.
<220> FEATURE:
<221> NAME/KEY: PEPTIDE
<222> LOCATION: (7)
<223> OTHER INFORMATION: Amino acid 7 is Xaa wherein Xaa = Asn, Orn, Ala
      or Nle.
<220> FEATURE:
<221> NAME/KEY: PEPTIDE
<222> LOCATION: (8)
<223> OTHER INFORMATION: Amino acid 8 is Xaa wherein Xaa = Met or Leu.
<220> FEATURE:
<221> NAME/KEY: PEPTIDE
<222> LOCATION: (9)
<223> OTHER INFORMATION: Amino acid 9 is Xaa wherein Xaa = Arg or Lys.
<220> FEATURE:
<221> NAME/KEY: BINDING
<222> LOCATION: (5)..(9)

<400> SEQUENCE: 99

Cys Phe Xaa Xaa Xaa Xaa Xaa Xaa Xaa Lys Val Arg
 1               5                  10

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: a fragment
      of human lactoferrin consisting of the amino acids in
      positions 12 40

<400> SEQUENCE: 100

Val Ser Gln Pro Glu Ala Thr Lys Cys Phe Gln Trp Gln Arg Asn Met
 1               5                  10                  15

Arg Lys Val Arg Gly Pro Pro Val Ser Cys Ile Lys Arg
            20                  25

<210> SEQ ID NO 101
<211> LENGTH: 9
<212> TYPE: PRT
<213> ORGANISM: Artificial Sequence
<220> FEATURE:
<223> OTHER INFORMATION: of natural or artificial origin, corresponding
      to modification of the sequence consisting of amino
      acids 16 40 in human lactoferrin of SEQ ID NO. 2

<400> SEQUENCE: 101

Gly Pro Pro Val Ser Cys Ile Lys Arg
 1               5

<210> SEQ ID NO 102
<211> LENGTH: 4
<212> TYPE: PRT
<213> ORGANISM: Artificial Sequence
<220> FEATURE:
<223> OTHER INFORMATION: of natural or artificial origin, not a
      modification of the sequence consisting of amino
      acids 18 31 in human lactoferrin of SEQ ID NO. 99
```

```
<400> SEQUENCE: 102

Glu Ala Thr Lys
 1
```